US011377786B2

(12) United States Patent
Yang

(10) Patent No.: US 11,377,786 B2
(45) Date of Patent: Jul. 5, 2022

(54) SWEAT-ABSORPTIVE QUICK-DRYING COMPOSITION AND SWEAT-ABSORPTIVE QUICK-DRYING FABRIC CONTAINING FUNCTIONAL MICROCAPSULES

(71) Applicant: LASHEVAN KOREA CO., LTD, Changwon-si (KR)

(72) Inventor: See-Young Yang, Goyang-si (KR)

( * ) Notice: Subject to any disclaimer, the term of this patent is extended or adjusted under 35 U.S.C. 154(b) by 0 days.

(21) Appl. No.: 16/623,879

(22) PCT Filed: May 30, 2018

(86) PCT No.: PCT/KR2018/006118
§ 371 (c)(1),
(2) Date: Dec. 18, 2019

(87) PCT Pub. No.: WO2019/225792
PCT Pub. Date: Nov. 28, 2019

(65) Prior Publication Data
US 2021/0140101 A1     May 13, 2021

(30) Foreign Application Priority Data

May 21, 2018    (KR) ........................ 10-2018-0057595

(51) Int. Cl.
*D06M 23/12*       (2006.01)

(52) U.S. Cl.
CPC .................................. *D06M 23/12* (2013.01)

(58) Field of Classification Search
CPC ..................................................... D06M 23/12
See application file for complete search history.

(56) References Cited

FOREIGN PATENT DOCUMENTS

| JP | S62104978 | 5/1987 |
|----|-----------|--------|
| JP | H06123079 | 5/1994 |
| JP | 2017179633 | 10/2017 |
| KR | 1019860002171 | 12/1986 |
| KR | 100653757 | 12/2006 |

OTHER PUBLICATIONS

English Machine Translation KR100653757 (B1) obtained at: https://worldwide.espacenet.com/publicationDetails/description?CC=KR&NR=100653757B1&KC=B1&FT=D&ND=3&date=20061206&DB=EPODOC&locale=en_EP# (Year: 2005).*

* cited by examiner

*Primary Examiner* — Arrie L Reuther
(74) *Attorney, Agent, or Firm* — Schmeiser, Olsen & Watts, LLP

(57) ABSTRACT

The present invention relates to functional fibers, that is, sweat-absorptive quick-drying fibers through which moisture, such as sweat discharged from the skin, is quickly discharged to the outside to be dried. A sweat-absorptive quick-drying composition including a water repellent for fibers as a material applied on the fibers further includes water-repellent microcapsules and wasabi antibacterial microcapsules respectively obtained by performing micro-encapsulation of the water repellent for fibers and wasabi oil. Accordingly, it is possible to ensure a very stable water-repellent function by using a water-repellent-functional-processing agent subjected to micro-encapsulation treatment, unlike conventional fibers subjected to sweat-absorptive quick-drying treatment.

6 Claims, 9 Drawing Sheets

Moisture control properties of fibers ( AATCC 195 : 2017 )

| | Index | | Average | Grade |
|---|---|---|---|---|
| #1 | Absorption time (sec) | Upper side | 2.849 8 | - |
| | | Lower side | 2.662 4 | - |
| | Absorption rate (%/sec) | Upper side | 41.874 2 | - |
| | | Lower side | 57.729 | - |
| | Maximum absorption radius (mm) | Upper side | 21.0 | - |
| | | Lower side | 23.0 | - |
| | Diffusion speed (mm/sec) | Upper side | 4.395 4 | - |
| | | Lower side | 4.741 9 | - |
| | Unidirectional movement performance (%) | | 374.000 2 | - |
| | Total moisture control performance, OMMC | | 0.852 4 | 5 |

FIG. 2

Moisture control properties of fibers ( AATCC 195 : 2017 )

| | Index | | Average | Grade |
|---|---|---|---|---|
| #1 | Absorption time (sec) | Upper side | 2.737 4 | |
| | | Lower side | 3.018 8 | |
| | Absorption rate (%/sec) | Upper side | 56.572 3 | |
| | | Lower side | 33.250 4 | |
| | Maximum absorption radius (mm) | Upper side | 23.0 | |
| | | Lower side | 23.0 | |
| | Diffusion speed (mm/sec) | Upper side | 4.723 8 | |
| | | Lower side | 4.436 3 | |
| | Unidirectional movement performance (%) | | -335.792 3 | |
| | Total moisture control performance, OMMC | | 0.314 6 | 2 |

FIG. 3

| Test items | Test result |
| --- | --- |
| | Sample 1 |
| Antibacterial activity (%) : KS K 0693:2016 applies | |
| Antibacterial rate | |
| Test bacteria ① | 99.3 |
| Test bacteria ② | > 99.9 |

\* Note) 1. Test species :
        Test bacteria ① : Staphylococcus aureus ATCC 6538 (Staphylococcus aureus)
        Test bacteria ② : Klebsiella pneumoniae ATCC 4352 (Bacillus pneumoniae)

2. Concentration of solution containing inoculation bacteria :
        Test bacteria ① – $1.2 \times 10^5$ CFU/mL
        Test bacteria ② – $1.0 \times 10^5$ CFU/mL 3. Control specimen : Standard cotton cloth
  4. Nonionic surfactant :
        Tween 80, Addition of 0.05% of solution containing inoculation bacteria

FIG. 7

| Test items | Test result |
|---|---|
| | Sample 1 |
| Drying speed (min) : KS K 0642, 8.25.1:2016 A method | |
| | 260 |
| Absorption speed (min) : KS K 0642, 8.26.1:2016 B method Birack method | |
|   Wale direction (length) | 78 |
|   Course direction (width) | 75 |
| Deodorizing rate (%) : Gas detecting tube method | |
|   <Test time> | |
|     30min | 96 |
|     60min | 98 |
|     90min | 99 or more |
|     120min | 99 or more |
| * Note) 1. Test condition<br>    - Sample amount : 10cm X 10cm(1.7g)<br>    - Test gas : Ammonia($NH_3$)<br>    - Concentration of injected test gas : 500 μg/mL<br>    - Volume of container : 1000mL<br>  2. Test environment : Temperature 20°C , Humidity 65%<br>  3. Remarks :<br>    Deodorizing rate(%) = [ (Blank gas concentration - Sample gas concentration) / Blank gas concentration] X 100 | |

FIG. 8

SWEAT-ABSORPTIVE QUICK-DRYING COMPOSITION AND SWEAT-ABSORPTIVE QUICK-DRYING FABRIC CONTAINING FUNCTIONAL MICROCAPSULES

TECHNICAL FIELD

The present invention relates to a sweat-absorptive quick-drying composition containing functional microcapsules and a sweat-absorptive quick-drying fabric including the same.

BACKGROUND ART

Sweat-absorptive quick-drying fibers are functional fibers through which moisture, such as sweat discharged from the skin, is quickly discharged to the outside to be dried. That is, sweat-absorptive quick-drying fibers are fibers having a function of quickly absorbing moisture from a skin-contact side and then discharging the moisture to the outside so that a refreshed feeling is maintained while the fiber is being worn.

In order to manufacture fibers having such a sweat-absorptive quick-drying function, sweat-absorptive quick-drying fibers manufactured in various ways has been developed and are commercially available. Among them, in the case of the invention disclosed in Korean Patent No. 10-0653757 (Registration date: Nov. 28, 2006), fiber tissues of a skin-contact side (back layer) and a face layer have different components, and a difference in moisture absorption performance between the skin-contact area and the fibers of the face layer is used therein. Further, the above patent is a technology for realizing sweat-absorptive quick-drying performance by forming water-repellent layers on a predetermined area of the back layer at predetermined intervals to thus facilitate the discharge of moisture.

However, the application of the water-repellent layer using a simple combination of water-repellent components and the binder as described above realizes only the sweat-absorptive quick-drying function caused by uniform water repellency. Further, considerable difficulty and expense may be incurred in terms of processability compared to the effect expected to be obtained when functional fabrics having both hydrophilic and hydrophobic properties are processed.

DISCLOSURE

Technical Problem

Accordingly, an object of the present invention is to provide a smart sweat-absorptive quick-drying composition and fabric that are intelligent and responsive to the external environment in achieving the sweat-absorptive quick-drying properties. In particular, the present invention provides a sweat-absorptive quick-drying composition and fabric that are responsive to the external environment, in addition to having the properties of a conventional water-repellent processing agent, by utilizing the functions obtained through the micro-encapsulation of a water repellent.

Another object of the present invention is to provide a functional sweat-absorptive quick-drying composition and fabric having both antibacterial and deodorizing functions by performing processing using functional microcapsules that are capable of imparting a basic sweat-absorptive quick-drying function and a sustainable antibacterial property.

Technical Solution

Sweat-absorptive quick-drying fibers are mainly used for clothing, especially underwear, which frequently comes into direct contact with the skin. Due to these characteristics of use, both the function of quickly absorbing and rapidly drying the sweat discharged from the skin and the function of inhibiting bacterial propagation caused by retention of moisture such as sweat can be said to be required.

In accordance with the above requirement, in the method of processing the sweat-absorptive quick-drying fabric containing functional microcapsules according to the present invention, sustained-release microcapsules may be used, so that a core material inside the fabric is intelligently released depending on the external environment, that is, temperature or external impact. Further, when the sustained-release microcapsules are mixed with a conventional binder for coating fibers and then applied and printed on fibers, the microcapsules are slowly released from the inside of the binder polymer after the binder is fixed to the fibers.

Now, proposed is a method of processing fibrous fabrics which include the sustained-release water-repellent microcapsules to thus have an intelligent water-repellent function of sustainably responding to the external environment and further include functional antibacterial microcapsules containing a natural antibacterial component such as wasabi oil to thus have both antibacterial and deodorizing functions.

Accordingly, in order to accomplish the above objects, the present invention provides a sweat-absorptive quick-drying composition including a water repellent for fibers. The sweat-absorptive quick-drying composition includes water-repellent microcapsules and wasabi antibacterial microcapsules respectively obtained by performing micro-encapsulation of the water repellent for fibers and wasabi oil.

The sweat-absorptive quick-drying composition may include 5 to 20 wt % of the water repellent for fibers, 10 to 40 wt % of the water-repellent microcapsules, 2 to 5 wt % of the wasabi antibacterial microcapsules, 40 to 50 wt % of an aqueous binder for processing fibrous fabrics, and water as a remainder.

Meanwhile, the sweat-absorptive quick-drying composition may further include an aqueous penetrant.

In this case, the sweat-absorptive quick-drying composition may include 5 to 20 wt % of the water repellent for fibers, 10 to 40 wt % of the water-repellent microcapsules, 2 to 5 wt % of the wasabi antibacterial microcapsules, 0.1 to 1 wt % of the aqueous penetrant, 40 to 50 wt % of the aqueous binder for processing fibrous fabrics, and water as a remainder.

In addition, in order to accomplish the above objects, the present invention provides a sweat-absorptive quick-drying fabric obtained by coating a fibrous fabric with the sweat-absorptive quick-drying composition, followed by drying.

Advantageous Effects

According to the sweat-absorptive quick-drying composition and the fabric including the functional microcapsules according to the present invention, it is possible to ensure a very stable water-repellent function by using a water-repellent-functional-processing agent subjected to micro-encapsulation treatment, unlike conventional fibers subjected to sweat-absorptive quick-drying treatment.

Further, it is possible to ensure very stable functionality regardless of external conditions such as a pH and washing and also to ensure an intelligent sweat-absorptive quick-drying function that actively responds to the external environment and external impacts. That is, it is possible to process a sweat-absorptive quick-drying fiber having a sweat-absorptive quick-drying function that responds to external impacts (friction) and temperature. Further, it is

DESCRIPTION OF DRAWINGS

FIG. 2 shows the result of a test on fibers that are subjected to sweat-absorptive quick-drying treatment according to the embodiment of the present invention (a direction from a back side to a face side);

FIG. 3 shows the result of a test on fibers that are subjected to sweat-absorptive quick-drying treatment according to the embodiment of the present invention (a direction from a face side to a back side);

FIG. 7 shows a test report of the antibacterial activity of the fabric processed according to the embodiment of the present invention; and FIG. 8 shows a test report of the deodorizing ability of the fabric processed according to the embodiment of the present invention.

BEST MODE

Figure 1:
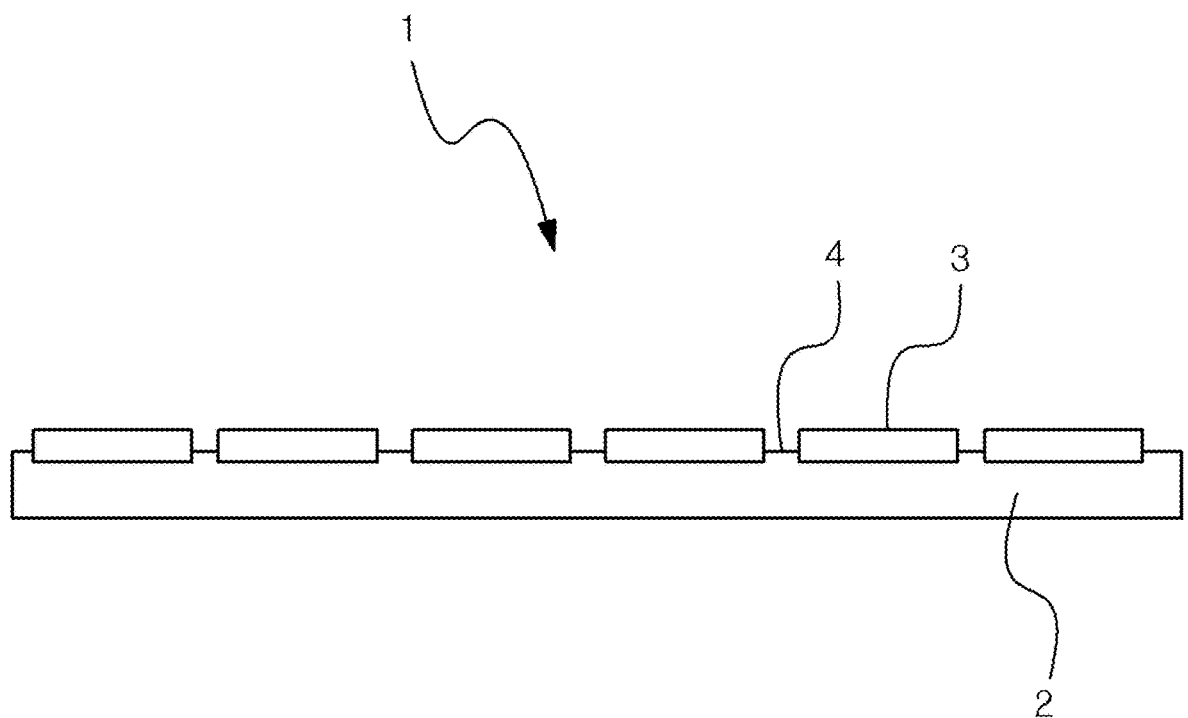
FIG. 1 is a cross-sectional view of a sweat-absorptive quick-drying fibrous fabric processed according to an embodiment of the present invention.

Horseradish (wasabi) is a plant belonging to the horseradish genus (wasabi genus) of the Cruciferae family and has a strong aroma and taste. The wasabi that is added to sushi or served with sashimi is a spice made from horseradish roots.

The main reason for using horseradish together with sashimi and sushi was because of the strong bactericidal and insecticidal effects of horseradish on parasites that are parasitic on fish. In particular, it is reported that allyl mustard-seed oil, which is a main component of a spicy taste, has bactericidal and insecticidal effects on several types of bacteria, fungal yeasts, aquatic bacteria, and parasites. Horseradish also has an excellent deodorizing function.

The spicy taste of horseradish is due to the sinigrin component thereof. The alkyl isothiocyanate component, which is the spicy taste component produced through the chemical reaction of the sinigrin component of horseradish, has antibacterial and bactericidal effects. However, due to the above-described characteristics of the horseradish and the volatilization characteristic thereof depending on the temperature, there is a problem in that it is difficult to achieve the same effect over a long period of time in a normal environment. Further, along with the above use precautions, the unique odor thereof may be unpleasant according to personal taste when used in an excessive amount. In other words, natural wasabi oil has excellent antibacterial activity when blended in an oil state for use, but it is difficult to directly process fibers and fabrics using wasabi oil in a natural oil state because the unique odor of wasabi oil may be unpleasant.

Therefore, in the present invention, in order to overcome the drawbacks caused by the use of natural wasabi and improve the excellent functions thereof, the wasabi oil is subjected to micro-encapsulation treatment using a sustained-release micro-encapsulation technique and is then used together with a general water repellent for fibers and a functional water repellent treated with sustained-release microcapsules, thereby overcoming the above usage limitations.

Meanwhile, a silicon-based water repellent, a fluorine-based water repellent, and a surfactant water repellent used in the treatment of fibers are materials for controlling the absorption of water by increasing a contact angle relative to water.

The fluorine-based water repellent is the most commonly used water repellent. In particular, the fluorine-based water repellent may exhibit both water repellency and oil repellency. Silicon-based water repellent is functionally poorer than fluorine-based water repellent, but is widely used in cotton poly and blends due to the soft texture thereof. However, water repellency is very sensitive to pH. In general, the water repellency function thereof is rapidly deteriorated when the pH is 9 or more or 4 or less.

For example, water-repellent work using a fluoro alkyl acrylated phosphorous ester co-polymer as the fluorine-based water repellent among the water repellents described above has been widely used. In the present invention, the silicon- or fluorine-based water repellent is first subjected to micro-encapsulation treatment, and then the water repellent subjected to the micro-encapsulation treatment is mixed with a conventional water repellent and used to thus achieve the maximum functional effect.

That is, a water-repellent coating solution containing the sustained-release microcapsules is applied in a predetermined pattern on a general fibrous fabric, thereby processing intelligent sweat-absorptive quick-drying fibers. The processed water-repellent microcapsules and wasabi antibacterial microcapsules may be mixed with an aqueous binder for processing fibers and then applied and printed on commercial fibrous fabrics.

It is preferable that the water-repellent microcapsules be used in a content of 50% or less based on the total blended materials. It is more preferable that the content be about 10 to 40%. When the content is 10% or less, it is difficult to expect the microcapsules to function properly. When the content is 40% or more, the content of microcapsules is excessively high, which may result in degradation of performance due to reduction of adhesion to fibers and weakening of the capsules to external impact.

It is preferable that the wasabi antibacterial microcapsules be used in a content of 10% or less based on the total blended materials. It is further preferable that the content be about 2 to 5%. When the content is 2% or less, there are concerns about degradation of antibacterial properties. When the content is 5% or more, an unpleasant feeling may be caused due to the unique odor of wasabi oil. When used within the above-described content range, sufficient antibacterial properties may be ensured.

It is preferable that the conventional silicon-based or fluorine-based water repellent that is not subjected to micro-encapsulation treatment be used in a content of about 5 to 20%.

An aqueous acryl- or urethane-based binder for fibrous fabric processing is used together with the blended materials of the above-described compounds, thus increasing adhesion to the fibers. The microcapsules are in the form of particles. In the case of such microcapsules in the form of particles, desired durability may be expected only when the microcapsules are physically attached to the fibrous fabric using a binder. As the binder that may be used together therewith, various binders such as aqueous acryl- or urethane-based binders may be used. A binder that is capable of maintaining sufficient adhesion force to the fibers after treatment of the fibrous fabric and has excellent resistance to washing may be selected for use.

In order to increase the penetrability of the blended materials to the fibers, the adhesion of the blended materials to the fibers, and the durability thereof, an aqueous penetrant may be added and used as needed during blending. In this Example, DYNOL 960, manufactured by Air Product company, was used. Such penetrants are not essential additive components, and whether or not the penetrant is used and the type of chemicals used may be adjusted depending on the fiber surface and processing processes. In general, the penetrant is used in a content of 0.1 to 1% based on the total blended materials.

The method of manufacturing the sweat-absorptive quick-drying composition containing the above components is as follows.

[Micro-Encapsulation Process]

Emulsification Process of Fluorine-Based Water Repellent 50 g of Scripset 520 (product manufactured by Solenis company) is dispersed in 950 g of water. 8 g of caustic soda is added thereto and slowly heated to 90° C. After that, the temperature is maintained for about 30 minutes to achieve complete dissolution. Thereafter, cooling is performed, followed by storage at room temperature.

500 g of the Scripset 520 solution manufactured above is added to a 2-liter beaker. A rotation speed is maintained at about 800 rpm using a high-speed homomixer. 250 g of a fluoro alkyl acrylated phosphorous ester co-polymer, which is a fluorine-based water repellent, is slowly added thereto for about 10 minutes. After the completion of addition, the agitation speed of the homomixer is increased to 1200 to 1700 rpm, thus performing emulsification.

Emulsification Process of Wasabi Oil 50 g of Scripset 520 (product manufactured by Solenis company) is dispersed in 950 g of water. 8 g of caustic soda is added thereto and slowly heated to 90° C. After that, the temperature is maintained for about 30 minutes to achieve complete dissolution. Thereafter, cooling is performed, followed by storage at room temperature.

500 g of the Scripset 520 solution manufactured as described above is added to a 2-liter beaker. A rotation speed is maintained at about 800 rpm using a high-speed homomixer. 25 g of natural wasabi oil and 225 g of soybean oil (oil amount: 250 g) are slowly added thereto for about 10 minutes. After the completion of addition, the agitation speed of the homomixer is increased to 1200 to 1700 rpm, thus performing emulsification.

Composition and Preparation of Initial Condensation Polymer of Melamine 125 g of water is added to a 500 ml beaker. 50 g of 35% formalin, 70 g of melamine powder, and 7 g of urea are added thereto. The temperature is slowly increased while the blended materials are sufficiently agitated. Heating is performed with agitation for about 10 to 15 minutes until the temperature reaches about 60° C.

Micro-Encapsulation of Water Repellent

The prepared initial condensation polymer of melamine is added to the emulsifying reactor of the fluorine-based water repellent prepared as described above. The temperature is then increased to 70° C. while maintaining at least 1200 rpm.

A sufficient agitation state is maintained while checking the increase in viscosity as the reaction proceeds. After about 1 hour, a homomixer is removed, and agitation is continued for 5 hours or more using a typical agitator so that the temperature is maintained and the agitation speed is maintained at 500 to 1000 rpm.

Thereafter, heating is stopped, and 30 g of 5% citric acid solution is slowly added. Agitation is continued until the temperature is reduced to room temperature.

Figure 4:
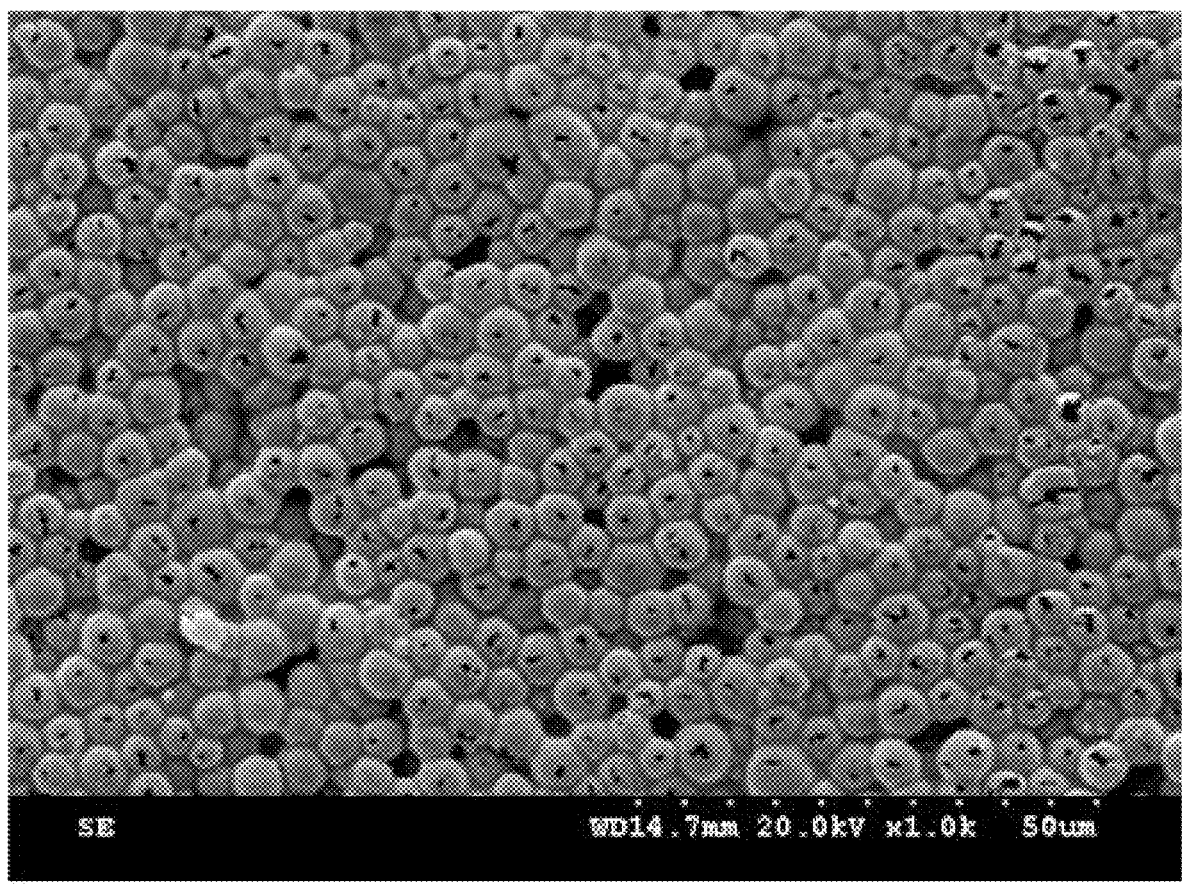
FIG. 4 is a 1000-times magnified photograph of the water-repellent microcapsules (wasabi antibacterial microcapsules) obtained using a micro-encapsulation process according to the embodiment of the present invention.
Figure 5:
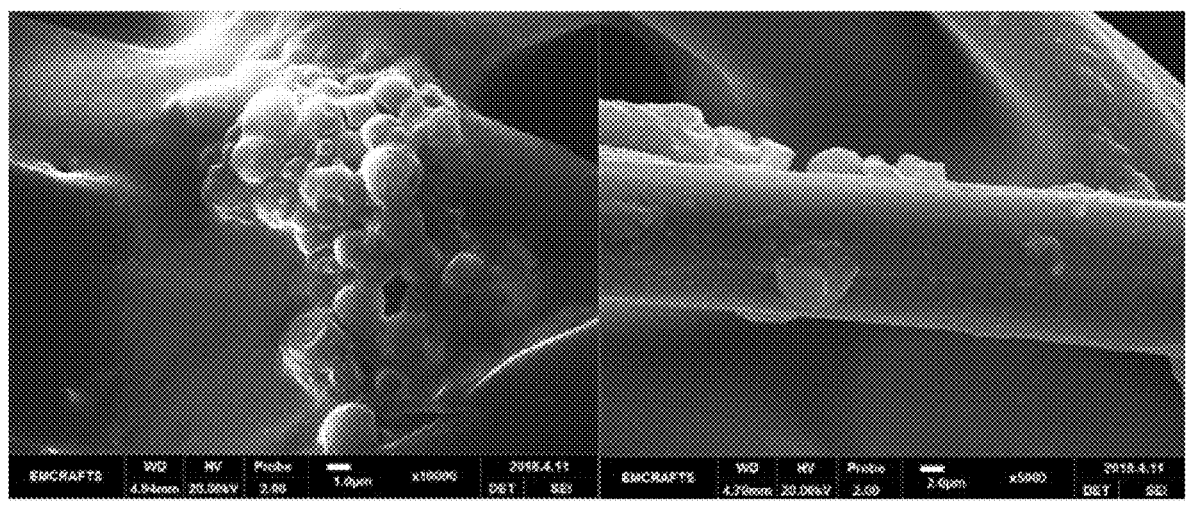
FIG. 5 is a 1000-times magnified photograph of the fibrous fabric coated with the water-repellent microcapsules (wasabi antibacterial microcapsules) obtained using a micro-encapsulation process according to the embodiment of the present invention.

The water-repellent microcapsules (see FIG. 4) thus obtained are stored until use.

Micro-Encapsulation of Wasabi Oil

The prepared initial condensation polymer of melamine is added to the emulsifying reactor of the wasabi oil prepared as described above. The temperature is then increased to 70° C. while maintaining at least 1200 rpm.

A sufficient agitation state is maintained while checking the increase in viscosity as the reaction proceeds. After about 1 hour, a homomixer is removed, and agitation is continued for 5 hours or more using a typical agitator so that the temperature is maintained and the agitation speed is maintained at 500 to 1000 rpm.

Thereafter, heating is stopped, and 30 g of 5% citric acid solution is slowly added. Agitation is continued until the temperature is reduced to room temperature.

The wasabi antibacterial microcapsules (see FIG. 4) thus obtained are stored until use.

[Blending Process]

Blending 1.

30% of the water-repellent microcapsules and 5% of the wasabi antibacterial microcapsules that were manufactured as described above, 10% of a fluorine-based water repellent, 50% of an aqueous acrylic binder, 0.2% of a penetrant, and water were added and mixed sufficiently.

Blending 2.

The same procedure as Blending 1 was performed, except that 40% of the water-repellent microcapsules, 5% of the wasabi antibacterial microcapsules, 10% of the fluorine-based water repellent, 40% of the aqueous acrylic binder, and 0.5% of the penetrant were used.

Blending 3.

The same procedure as Blending 1 was performed, except that 10% of the water-repellent microcapsules were used.

Blending 4.

The content of the water-repellent microcapsules was reduced to 5% to perform blending.

Blending 5.

Only the fluorine-based water repellent was blended as shown in the following table, without using the water-repellent microcapsules.

The compositional ratio of each of the components of Blending 1 to Blending 5 is shown in the following [Table 1].

TABLE 1

|  | Blending 1 | Blending 2 | Blending 3 | Blending 4 | Blending 5 |
|---|---|---|---|---|---|
| Water-repellent microcapsules | 30 | 40 | 10 | 5 |  |
| Wasabi antibacterial capsules | 5 | 5 | 5 | 2 |  |
| Fluorine-based water repellent | 10 | 10 | 10 | 10 | 15 |
| Aqueous acrylic binder | 50 | 40 | 50 | 50 |  |
| Penetrant | 0.2 | 0.5 | 1 | 1 |  |
| Water | 3.8 | 4.5 | 24 | 32 | 85 |
| Total | 100 | 100 | 100 | 100 | 100 |

[Fiber Treatment Process]

This is a process of processing a fibrous fabric using the sweat-absorptive quick-drying composition obtained through the above-described blending.

As the coating method, a method such as screen printing or gravure coating may be used. The method is not limited to any specific coating method, as long as the method is a printing method in which a predetermined pattern is formed on fibers. It is preferable to perform the coating for each section at a regular interval of about 0.5 to 1 mm between the patterns if circumstances allow. After the coating treatment, sufficient drying treatment is performed using a tenter or a drying apparatus, thereby completing the process.

The sweat-absorptive quick-drying performance of the fabric that has undergone the fiber treatment process as described above is shown in the following [Table 2].

TABLE 2

|  | Blending 1 | Blending 2 | Blending 3 | Blending 4 | Blending 5 |
|---|---|---|---|---|---|
| Initial sweat-absorptive quick-drying performance | 5th grade | 5th grade | 5th grade | 5th grade | 5th grade |
| Sweat-absorptive quick-drying performance after washing 30 times | 5th grade | 5th grade | 3rd to 4th grade | 2nd to 3rd grade | 1st to 2nd grade |
| Antibacterial activity | 99% | 99% | 99% | 99% | X |
| Deodorizing property after washing 30 times | 99% | 99% | 99% | 99% | X |

As can be seen in [Table 2], the initial sweat-absorptive quick-drying performance was the same for all of Blending 1 to Blending 5, specifically the fifth grade. However, as washing was repeated, the sweat-absorptive quick-drying performance of Blending 1 to Blending 3 was maintained without change, but the sweat-absorptive quick-drying performance of Blending 4 and Blending 5 was significantly reduced.

FIG. 1 shows a sweat-absorptive quick-drying fabric 1, and the surface of a fibrous fabric 2 is coated with a sweat-absorptive quick-drying composition 3 and dried using the fiber treatment process.

FIG. 2 shows the result of a test on fibers that are subjected to the sweat-absorptive quick-drying treatment as described above. It can be confirmed that water repellency in a direction from the back side (the upper side of FIG. 1) to the face side (the lower side of FIG. 1) of the fabric (see Attachment Document 1) is excellent, namely the fifth grade. In contrast, as shown in FIG. 3, it can be confirmed that water repellency in a direction from the face side (the lower side of FIG. 1) to the back side (the upper side of FIG. 1) (see Attachment Document 2) is poor, namely the second grade. That is, it can be seen that the sweat-absorptive quick-drying fabric 1 has unidirectional sweat-absorptive quick-drying performance.

Figure 6A:
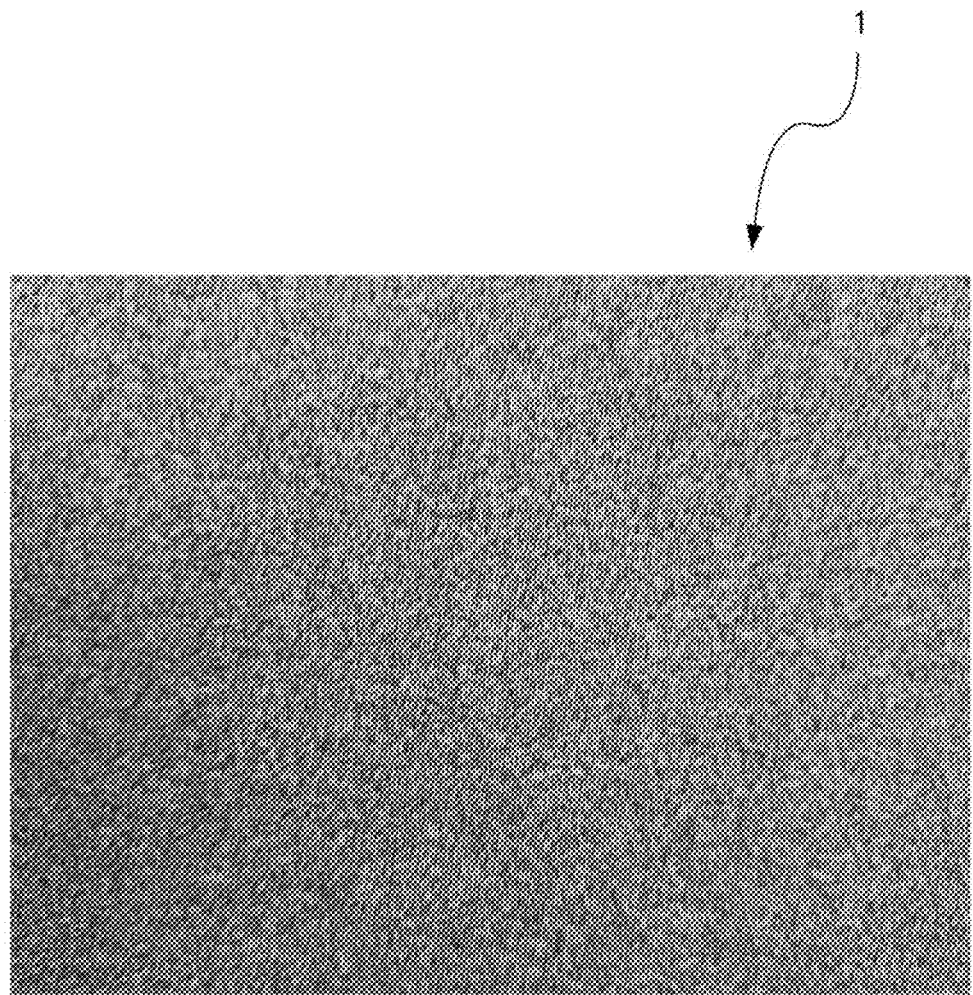
FIGS. 6A and 6B are photographs showing the surface of the fabric (back side) subjected to sweat-absorptive quick-drying processing according to the embodiment of the present invention before and after water spraying.
Figure 6B:
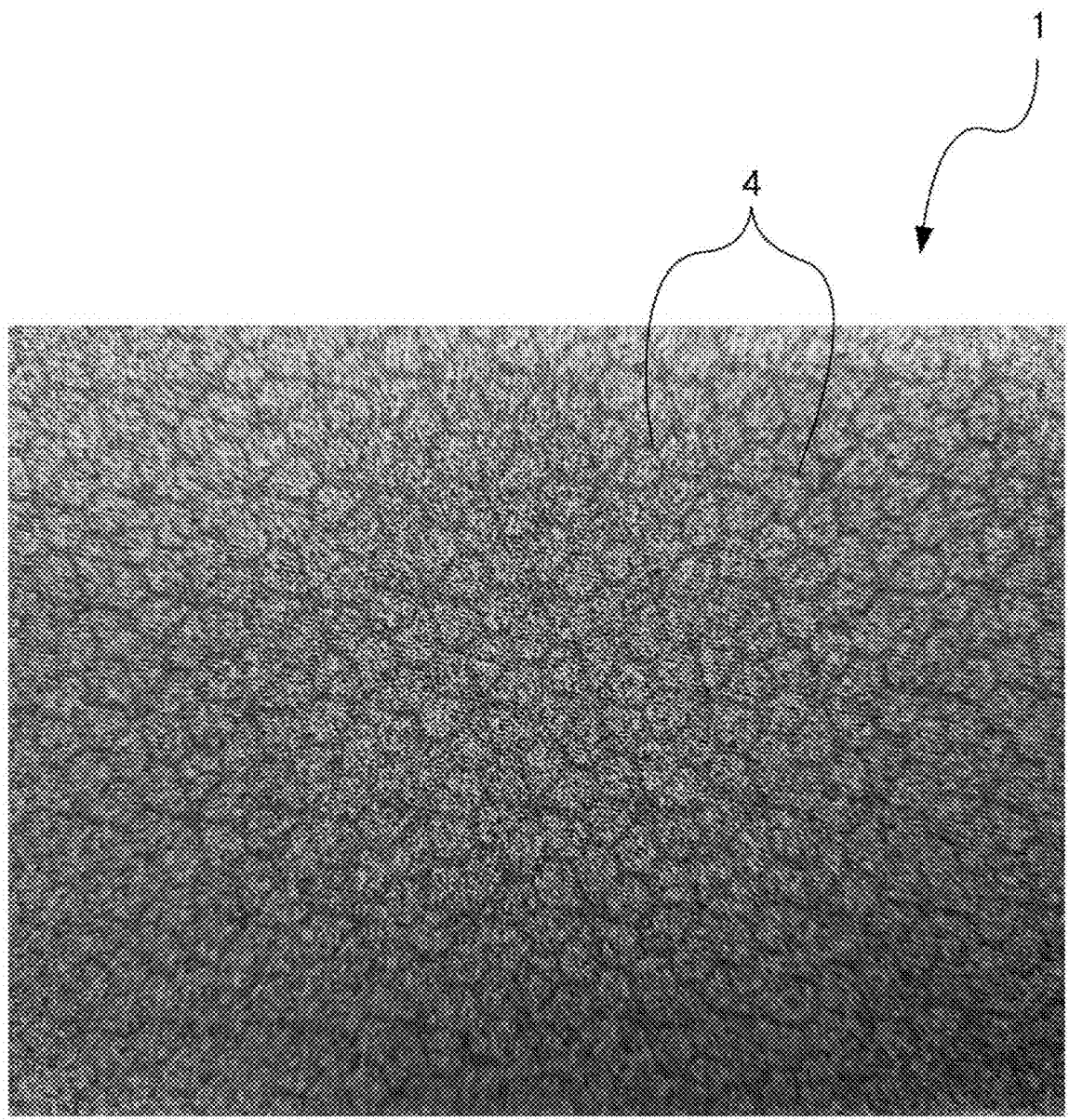

When water (simulating sweat during wearing) is sprayed on the back side (corresponding to the upper side of FIG. 1) of the sweat-absorptive quick-drying fabric 1 as shown in FIG. 6A, the water is drained, that is, water is repelled, as shown in FIG. 6B, in a space 4 (see FIG. 1) between coating surfaces 3, whereby the water smoothly moves toward the face side (corresponding to the lower side of FIG. 1).

FIG. 7 shows the main content of a test report on the antibacterial activity of the sweat-absorptive quick-drying fabric 1 manufactured as described above (see Attachment Document 3), and FIG. 8 shows the main content of a test report on the deodorizing ability of the sweat-absorptive quick-drying fabric 1 (see Attachment Document 4). As shown in FIGS. 7 and 8, it can be confirmed that the antibacterial activity and deodorizing ability of the sweat-absorptive quick-drying fabric 1 according to the present invention are excellent.

Meanwhile, since the sweat-absorptive quick-drying composition and sweat-absorptive quick-drying fabric described above are merely examples for better understanding of the present invention, it is not to be understood that the scope or the technical scope of the present invention is limited to those described above.

The scope or the technical scope of the present invention is defined by the claims and equivalents described below.

The invention claimed is:

1. A sweat-absorptive quick-drying composition including a water repellent for fibers, the sweat-absorptive quick-drying composition comprising:
    water-repellent microcapsules and wasabi antibacterial microcapsules respectively obtained by performing micro-encapsulation of the water repellent for fibers and wasabi oil.

2. The sweat-absorptive quick-drying composition of claim 1, further comprising:
    an aqueous penetrant.

3. The sweat-absorptive quick-drying composition of claim 2, wherein the sweat-absorptive quick-drying composition includes 5 to 20 wt % of a water repellent for fibers, 10 to 40 wt % of water-repellent microcapsules, 2 to 5 wt % of wasabi antibacterial microcapsules, 0.1 to 1 wt % of the aqueous penetrant, 40 to 50 wt % of an aqueous binder for processing fibrous fabrics, and water as a remainder.

4. A sweat-absorptive quick-drying fabric obtained by coating a fibrous fabric with the sweat-absorptive quick-drying composition of claim 3, followed by drying.

5. The sweat-absorptive quick-drying composition of claim 1, wherein the sweat-absorptive quick-drying composition includes 5 to 20 wt % of the water repellent for fibers, 10 to 40 wt % of the water-repellent microcapsules, 2 to 5 wt % of the wasabi antibacterial microcapsules, 40 to 50 wt % of an aqueous binder for processing fibrous fabrics, and water as a remainder.

6. A sweat-absorptive quick-drying fabric obtained by coating a fibrous fabric with the sweat-absorptive quick-drying composition of claim 5, followed by drying.

* * * * *